United States Patent [19]

Yeh et al.

[11] Patent Number: 4,767,524

[45] Date of Patent: Aug. 30, 1988

[54] VIRTUAL IMPACTOR

[75] Inventors: Hsu-Chi Yeh; Bean T. Chen; Yung-Sung Cheng; George J. Newton, all of Albuquerque, N. Mex.

[73] Assignee: Lovelace Medical Foundation, Albuquerque, N. Mex.

[21] Appl. No.: 81,928

[22] Filed: Aug. 5, 1987

[51] Int. Cl.$^4$ ............................................. B07B 7/00
[52] U.S. Cl. .................................... 209/143; 55/270; 73/28; 209/133
[58] Field of Search ............... 209/132, 133, 142, 143, 209/138, 139.1, 134, 135; 55/270; 73/28, 863.21, 865.5

[56] References Cited

U.S. PATENT DOCUMENTS

| | | | |
|---|---|---|---|
| 3,315,806 | 4/1967 | Sigwart et al. | 209/143 |
| 3,724,658 | 4/1973 | Stephenson | 209/143 |
| 3,731,464 | 5/1973 | Brumbaugh et al. | 209/143 X |
| 3,854,321 | 12/1974 | Dahneke | 73/28 |
| 3,954,428 | 5/1976 | Marple et al. | 73/28 X |
| 4,132,894 | 1/1979 | Yule | 73/28 X |
| 4,301,002 | 11/1981 | Loo | 209/143 |
| 4,358,302 | 11/1982 | Dahneke | 55/270 X |
| 4,545,897 | 10/1985 | Masuda | 209/143 X |
| 4,670,135 | 6/1987 | Marple et al. | 209/143 |
| 4,689,052 | 8/1987 | Ogren et al. | 55/270 X |

FOREIGN PATENT DOCUMENTS

| | | | |
|---|---|---|---|
| 1015882 | 1/1966 | United Kingdom | 209/143 |
| 0285327 | 1/1971 | U.S.S.R. | 73/28 |
| 0857791 | 8/1981 | U.S.S.R. | 73/28 |

OTHER PUBLICATIONS

"Particle Collection Characteristics of a Single-Stage Dichotomous Sampler", McFarland et al., Environmental Science & Technology, vol. 12, No. 6, Jun. 1978.

Primary Examiner—Robert B. Reeves
Assistant Examiner—Edward M. Wacyra
Attorney, Agent, or Firm—Nilsson, Robbins, Dalgarn, Berliner, Carson & Wurst

[57] ABSTRACT

A virtual impactor having improved efficiency and low wall losses in which a core of clean air is inserted into the aerosol flow while aerosol flow is maintained adjacent inner wall surfaces of the focusing portion of the impactor. The flow rate of the core and the length of the throat of the impactor's collection probe, as well as the dimensional relationships of other components of the impactor adjacent the separation region of the impactor, are selected to optimize separation efficiency.

16 Claims, 3 Drawing Sheets

VIRTUAL IMPACTOR

GOVERMENT SUPPORT

This invention was made with Government support under Contract DE-AC04-76EV01013 awarded by the U.S. Department of Energy. The Government has certain rights in this invention.

BACKGROUND OF THE INVENTION

Conventional cascade impactors have been used extensively for fractionating airborne particles according to their aerodynamic sizes, enabling the size distribution to be determined by analyzing the collected particles. However, this technique has several inherent problems, including stage overloading and particle reentrainment, and introduces errors in the measured aerodynamic size distribution. In addition, aerodynamically separated aerosols cannot be used directly as a source of monodisperse aerosols, because the particles have been collected on the impactor stages. It is also not possible to take either the coarse or fine particle output of one stage and use it as the input of a second stage for obtaining increased narrow sized fraction of the separated particle stream.

These limitations are avoided in the dichotomous virtual impactor. This device uses the same principle of inertial separation, but the impaction plate is replaced by a region of relatively stagnant air contained in the cavity of a receiving probe. A virtual surface is formed by deflected streamlines that are similar to those in conventional solid plate impactors. The fine particles follow the streamlines of the major air flow, while the coarse particles, with greater inertia, pass into the forward minor flow region. Both size fractions can, subsequently, be ducted for any desired methods of analysis or collections, including direct-reading, continuous instrumentation, or can be sent to a subsequent stage or stages for further refinement.

Because a virtual impactor does not collect particles, but merely redirects them into two different air streams according to the cutoff characteristic, it is generally free from problems of particle bounce and reentrainment that often occurs in other inertial, size separating devices. However, in drawing minor flow through the receiving or collection probe, the coarse particle flow entrains a small amount of fine particles. This contamination is an intrinsic disadvantage of virtual impactors of conventional design.

Masuda, et al, in the publication "An Improved Virtual Impactor for Particle Classification and Generation of Test Aerosols With Narrow Size Distributions", J. Aerosol Sci Vol. 10 pp 275-287 (1979) described a virtual impactor that reduced contamination by confining the input aerosol flow between an inner and an outer flow of particle-free air. However, under certain operating conditions, apparent distortions in the annular flow of the aerosol may exist, adversely affecting separation efficiency. More particularly, Masuda, et al. found that with their configuration, if the ratio of outer clean air flow rate to total flow rate exceeded 0.2, separation fell below predicted values. Masuda, et al. explained this behavior on the basis of distortion of the annular aerosol flow. This instability is a serious detriment to utilization of the Masuda, et al. structure.

As is the case with real impactors, the two parameters used to characterize the performance of a virtual impactor are separation efficiency and wall loss. A good virtual impactor should have a sharp separation curve with little wall loss and little fine particle contamination in the coarse particle fraction. While Masuda, et al. attempted to address the problem of separation efficiency, other strategies are needed to reduce the wall losses. Loo U.S. Pat. No. 4,301,002 describes a variety of dimensional relationships between the components of an acceleration nozzle and collection probe of a virtual impactor and such parameters are also described by Chen, et al. in the article "A Novel Virtual Impactor: Calibration and Use", J. Aerosol Sci. Vol. 16, No. 4, pp. 343-354 (1985). Achievement of an optimum design requires balancing between the movement of the various particle and gas streams and spacing and sizing of the confronting components to obtain both low wall loss and good separation efficiency.

SUMMARY OF THE INVENTION

The present invention provides an improvement in virtual impactor design which utilizes a clean air core to obtain high separation efficiency, but without the instability problems of Masuda, et al. Various flow characteristics and dimensional characteristics are selected and balanced against each other to obtain a virtual impactor with both small wall losses, less than 5%, and little or no fine particle contamination of the coarse particle flow. The design characteristics of the present invention provide excellent results for both solid and liquid aerosols. The virtual impactor has an acceleration nozzle and a collection probe, each aligned about the same predetermined linear axis, and a flow separation region therebetween. The acceleration nozzle comprises an inlet, a substantially narrower outlet orifice, and a flow focusing portion between the inlet and outlet formed with an inner wall surface shaped for converging the aerosol flow from the inlet toward the linear axis whereby the converged aerosol flows through the outlet orifice to the flow separation region. The collection probe has an inlet opening centered on the linear axis.

The present invention provides an improvement to such a virtual impactor by providing means for flowing clean air, or purified inert gas, more generally gas of near zero or zero aerosol content, into the center of the aerosol flow. The core of clear gas converges with the aerosol flow and flows therewith through the outlet orifice of the nozzle, encased by the aerosol while the flow of aerosol is maintained adjacent the inner wall surface of the focusing portion of the nozzle. Importantly, no sheath is formed to sandwich the aerosol between clean air components. Rather, the flow of the aerosol is adjacent to the wall surface of the focusing portion, clean air being injected only into the center of the aerosol. This enables a substantial increase in separation efficiency with a high degree of stability. More particularly, contamination can be minimized and substantially eliminated by providing a flow rate of core gas that is larger than (preferably more than 1.2 times) the rate of the coarse particle flow. By utilizing only a clean air core and not a sheath, such a flow rate can be achieved without a loss of stability.

In a more particular embodiment, for example, the acceleration nozzle includes a laminator at its inlet and the clear core gas is injected into the center of the aerosol by means of a conduit protruding into the acceleration nozzle inlet downstream and centrally of the laminator.

Specific dimensional relationships have been found to minimize wall losses and in conjunction with the clean air core optimize the performance of the impactor. Using the letter "W" to represent the inner diameter of the acceleration nozzle outlet orifice at the separation region, preferred dimensions of certain components of the virtual impactor can be expressed as a multiple of that dimension. Thus, the length of the throat of the inner portion of the collection probe preferably has a dimension of at least 0.3 W. The outer diameter of the collection probe at the separation region preferably has a dimension of less than 5 W. The shoulder of the impaction opening of the collection probe is preferably rounded and preferably has a ratio of at least 0.1 W. The outer diameter of the nozzle outlet orifice at the separation region is preferably less than 5 W. The inner diameter of the collection probe at the separation region is preferably in the range of at least 1 W to about 1.8 W. The length of the flow separation region is preferably in the range of about 0.5 W to 1.5 W. The length of the outlet orifice of the acceleration nozzle is preferably in the range of about 0.5 W to 1.5 W. In addition, the angle of the inner wall surface of the focus portion of the nozzle relative to the linear axis is preferably in the range of about 20 degrees to about 60 degrees.

BRIEF DESCRIPTION OF THE DRAWINGS

FIG. 2 is an elevation sectional, partially schematic, view of a virtual impactor embodying the invention;

FIG. 3 is a schematic elevation sectional view of the outlet orifice of the acceleration nozzle showing the aerosol/clean air flow in the nozzle.

DETAILED DESCRIPTION OF THE INVENTION

Figure 1:
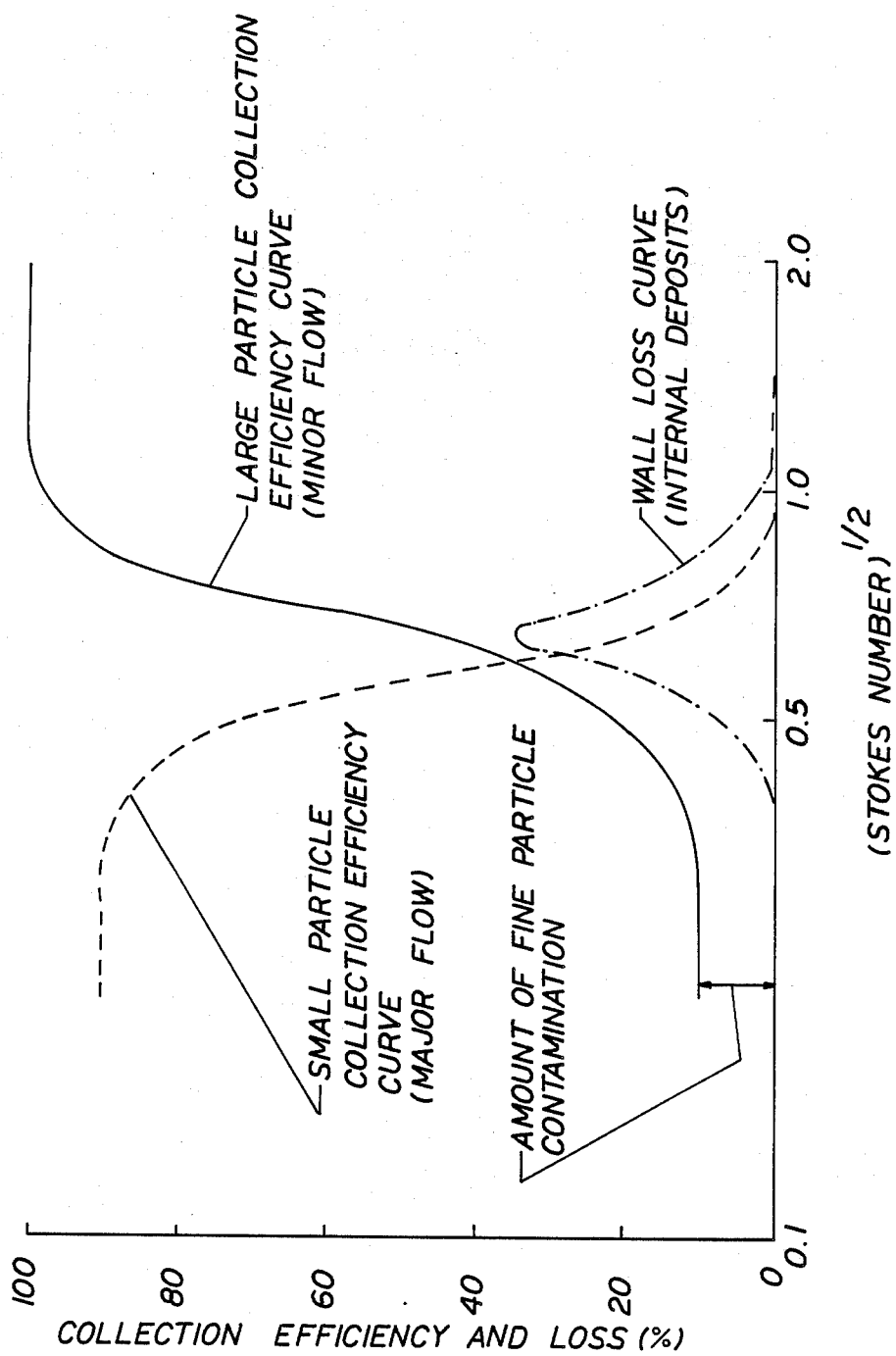
FIG. 1 is a plot of the collection efficiency and internal loss curves in a typical virtual impactor of the prior art.

FIG. 1 shows the collection (or separation) efficiency and wall loss of a conventional virtual impactor. In comparing efficiencies among different impactors, it is conventional to use the square root of the Stokes number which is a dimensionless particle diameter that is a function of the aerodynamic particle size. Specifically:

$$Stk = D_{AE}^2 C V_O / 9\mu W$$

where $D_{AE}$ is the aerodynamic particle size, C is the particle slip correction factor, $V_O$ is the mean fluid velocity at the nozzle throat, $\mu$ is the fluid viscosity, and W is the diameter of the acceleration nozzle outlet orifice. It is also conventional to refer to the square root of the Stokes number that corresponds to a separation efficiency of 50%, i.e., $(Stk)_{50}^{\frac{1}{2}}$, in comparing virtual impactors.

With this in mind, curve 1 of FIG. 1 shows the percent of particles exiting the acceleration nozzle of a conventional virtual impactor which are carried to the inlet opening of minor flow. Curve 2 shows the percentage of particles that are drawn outward in a radial direction by the major flow. Curve 3 shows the percentage of particles that collide with the internal physical surfaces, resulting in wall loss. These three curves, especially curves 1 and 8, are typically used to characterize the performance of a virtual impactor. The maximum of the wall loss curve is shown at the size approximately corresponding to $(Stk)_{50}^{\frac{1}{2}}$, reflecting the tendency for particles of the cutoff size to be intercepted near the separation region, such as the probe surface which deflects the stream lines. Because wall loss would result as an apparent separation efficiency and subsequent particle bounce and reentrainment could, especially with solid aerosols, deteriorate the consistency of the separation curve, especially at the cutoff region, the value of $(Stk)_{50}^{\frac{1}{2}}$ cannot be accurately estimated. Wall loss should therefore be reduced to a minimum to have a good virtual impactor with predictable cutoff characteristics.

Another criteria for a good virtual impactor is the extent to which the fine particle contamination is minimized. This is readily detected from FIG. 1 in which the values in curve 1 do not reach zero for small values of the square root of the Stokes number. Expressed differently, the corresponding efficiency values in curve 2 do not reach unity.

Figures 2, 3:
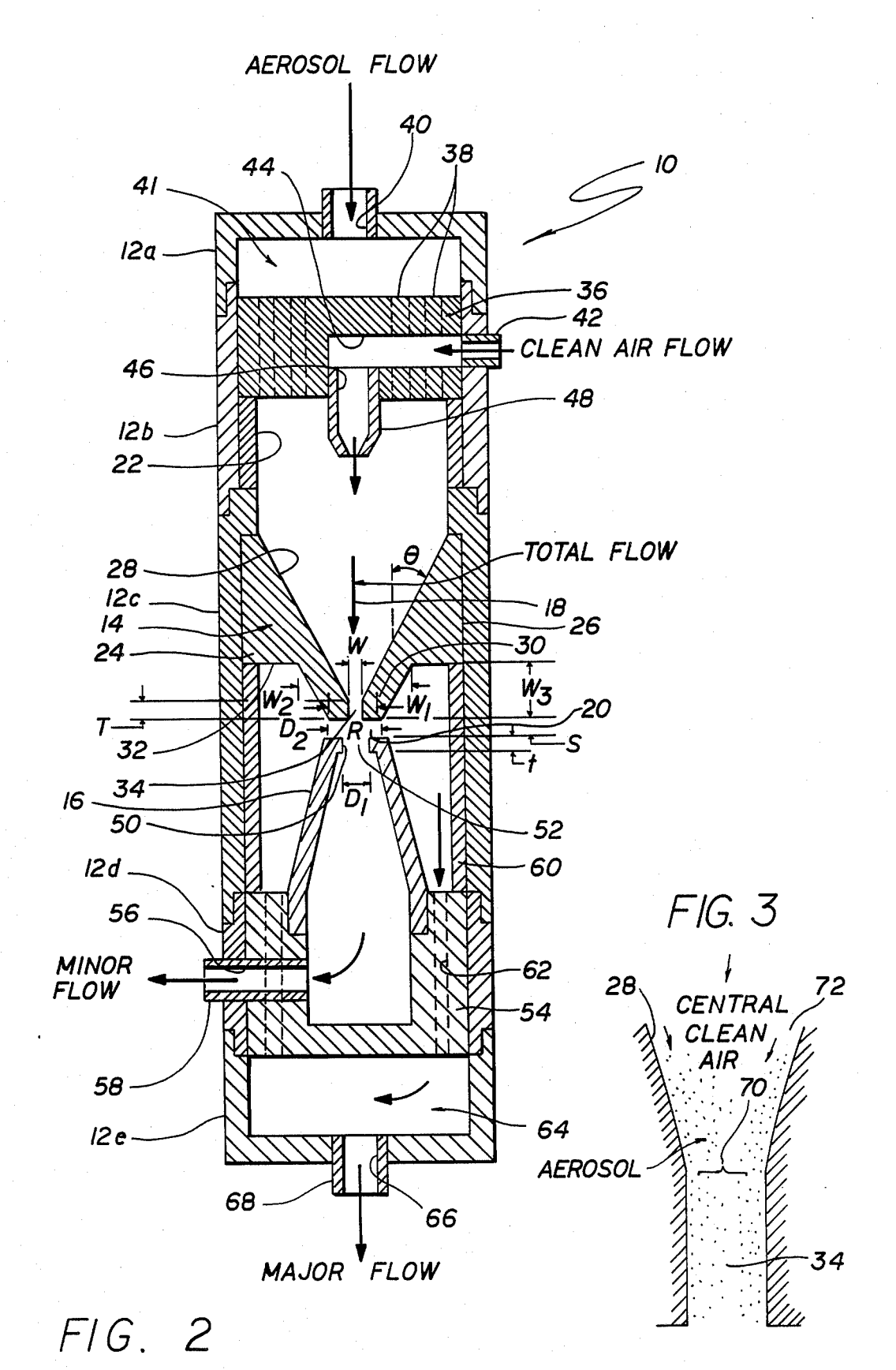

Referring to FIG. 2, a virtual impactor of the present invention is shown which has less than 5% wall losses and little or no fine particle contamination of the minor, coarse particle flow, with both solid and liquid aerosols. The virtual impactor 10 includes five sections of cylindrical housing 12a-d in which is disposed a cylindrical acceleration nozzle 14 and a collection probe 16, each aligned about the same predetermined linear axis 18 and defining between them a flow separation region 20. All sections are tightly threaded with O-ring seals (not shown) to prevent air leakage. The acceleration nozzle region 14 includes a cylindrical inlet section 22, about one inch in length, carried above a focusing member 24. The focusing member 24 is formed with a cylindrical outer wall 26 and a conical inner wall 28. The acceleration nozzle 14 includes a mouth portion 30 which is formed as a continuation of the conical wall 28 and a corresponding portion of the bottom wall 32 of the nozzle 14. The acceleration nozzle 14 terminates in an outlet orifice 34 at the bottom of the conical wall 28.

Within the housing 12b is disposed a cylindrical laminator 36 above, and supported by, the inlet spacer section 22. The laminator 36 is formed of a plurality of tubular conduits 38 sufficiently numerous and narrow to assure laminar flow to the impactor. For example, there are about 30 such conduits each about $\frac{1}{8}$ inch in diameter. The top of the housing is formed with an inlet, shown schematically at 40. The housing 12a forms a space 41 above the laminator 36 serving as a manifold region for the inlet 40. Tubulation 42 for the flow of clean air extends to a conduit 44 through the laminator 36, making a right turn downwardly, as indicated schematically at 46, to continue as a conduit 48 protruding into the acceleration nozzle inlet section 22 downstream of the laminator 36. The clean air conduit 48 is disposed such that the laminator 86 is centered on the conduit 48. A source of flowing gas having near zero aerosol content, e.g., clean air, is connected to the tubulation 42.

The collection probe 16 is formed at its upper end with an annular inner wall surface 50 defining a collection probe inlet serving as an impaction opening 52. The collection probe extends conically outwardly from the impaction opening 52 to a receiving member 54. The receiving member 54 includes an outlet conduit 56 to which is connected outlet tubulation 58 for directing flow through the collection probe out of the impactor.

The receiving member 54 is a cylindrical solid and supports a cylindrical sleeve 60 that serves to separate and space the acceleration nozzle 14 from the collection probe 16. The left dimension of the cylindrical sleeve 60 serves, in conjunction with the geometry of the acceleration nozzle 14 and collection probe 16 to define the length of the flow separation region 20. The receiving member 54 is formed with a plurality of cylindrical openings 62 sufficiently sized as to not impede the flow of gas from the vicinity around the outside of the collection probe. A plenum region 64 located below the receiving member 54 leads to an exit conduit 66 and associated tubulation 68.

In operation, aerosol is drawn into the virtual impactor through the inlet 40 and laminarized by passage through the laminator conduits 38. Meanwhile, clean air passes through the clean air conduit 44 emerging centrally downstream of the laminator 86, resulting in aerosol flow with a core of clean air in the center. Flow is subsequently accelerated by the narrowing cross section of the acceleration nozzle 14, thus increasing the momentum of the aerosol particles. Finally, the particles are separated according to their aerodynamic diameters at the flow separation region 20 defined by the gap between the acceleration nozzle 14 and the collection probe 16. Fine particles follow the laterally deflected stream lines and leave the impactor with the major flow through the exit conduit 66, while coarse particles pass through the collection probe 16 at a relatively low flow rate and emerge from the outlet conduit 56 as a minor flow.

Referring to FIG. 3, there is shown a schematic diagram of the aerosol/clean air flow in the vicinity of the outlet orifice 34 of the acceleration nozzle. The clean air flow forms a central core 70 encased by the aerosol flow 72. Importantly, the aerosol flow is maintained adjacent the conical inner wall 28 of the focusing member 24. It is this configuration which supplies stability while enabling the high separation efficiency advantage of the clean air core 70. We have found that contamination of fine particles in the minor flow can not be eliminated when the flow rate of the central clean air is smaller than or equal to the minor flow rate. On the other hand, contamination is minimal when the flow rate of the clean air core 70 is equal to or larger than 1.2 times the minor flow rate.

In accordance with this invention, in conjunction with the provision of a stable clean air core, we have found certain preferred dimensional relationships that idealize the performance of the virtual impactor, particularly with respect to achieving low wall loss and increasing the sharpness of separation of particles about the cutoff point. These dimensional relationships are conveniently referenced to the dimension of the inner diameter of the nozzle outlet orifice 34 at the flow separation region 20, designated by the letter W in FIG. 2. Accordingly, in the following discussion, the dimensional relationship of various components of the virtual impactor will be expressed as a multiple of W.

Referring back to FIG. 2, the length t of the virtual impaction opening 50, defined by the annular inner wall surface at the inlet portion of the collection probe 16 (i.e., the throat length of the collection probe impaction opening) should be at least 0.3 W and preferably at least 0.8 W, with a practical maximum of about 2.6 W. With the throat length equal to 0, the separation efficiency curve becomes less steep around the cutoff region and loses its sharpness. This is due to the fact that in order to have a good separation, a certain throat length is required to extend the inertial separation into the uppermost portion of the collection probe 16. Contrary to implications from Loo U.S. Pat. No. 4,301,002, the configuration internally of the collection probe 16 downstream from the impaction opening 52 does not play an important role in terms of the inertial separation if the throat length is sufficiently long.

The outer surface diameter of the collection probe at the separation region, indicated by the designation $D_2$, should be less than 5 W. The efficiency curve around the cutoff size shifts to the right with a steeper cutoff characteristic for smaller values of $D_2$. Additionally, particularly for solid particles, it is advantageous to coat the top surface of the collection probe 16 with a low friction material such as grease so as to reduce the effect of particle bounce, although with low wall losses this effect is not profound. Petroleum derived grease can be used or any low friction synthetic material. For liquid particles, the drops as deposited stick to the interface surface and the bounce effect is not significant. However, with solid particles, because the particles of cutoff size dominate internal losses, the separation efficiencies for these particles are smaller without a grease-coated probe, than with a grease-coated probe, but the difference is small due to low wall losses.

Preferably, the impaction opening 52 of the collection probe 16 is defined by a rounded shoulder, in particular with a radius of at least 0.1 W, up to 0.5 W, preferably at least 0.3 W. With a square shoulder (R=0), particles are found to be deposited on the shoulder surface because the shoulder cannot provide a smooth return for some of the deflected, major flow streamlines which may penetrate slightly into the collection probe 16. The deposits become less for R=0.1 W and almost disappear for R=0.3 W, indicating that a dimension of 0.3 W has a suitable roundness for those deflected streamlines. However, with a substantially larger R, back impaction on the lower surface of the acceleration nozzle outlet orifice becomes significant. These losses are reduced by decreasing the outer diameter of the nozzle outlet orifice 34, at the separation region, indicated by the letter $W_1$, to a dimension of less than 5 W, down to about 1.5 W. The combination of increased R and decreased $W_1$ reduces losses on the acceleration nozzle surfece to less than 1% for aerosols around the cutoff size.

The angle of the inner wall surface 28 of the focus and acceleration portion of the acceleration nozzle 14 relative to the linear axis should be in the range of about 20 degrees to about 60 degrees.

Other dimensions are not as critical to the operation of the virtual impactor 10. The inner diameter of the collection probe 16 at the flow separation region 20 is indicated by the letter $D_1$ and should be in the range of about 1 to about 1.8 W. The length of the flow separation region should be in the range of about 0.5 to about 1.5 W. The annular inner wall surface defining the outlet orifice of the acceleration nozzle (i.e., the throat length of the acceleration nozzle) is indicated by the letter T, and should have a dimension in the range of about 0.5 W to about 1.5 W.

In a particular embodiment, a virtual impactor of the present invention has been constructed with the diameter of the nozzle outlet orifice, W, equal to 3.05 mm. Practical devices can be constructed with W ranging from 0.5 mm to about 10 mm, depending on the desired cutoff particle size and total flow rate. At W=3.05, mm with total flow rate of 8 L/min, the ratio of minor flow to total flow was 8% and the ratio of clean air flow to total flow was 18%, with a cutoff particle size of about 4.4 microns in aerodynamic diameter.

Figure 4:
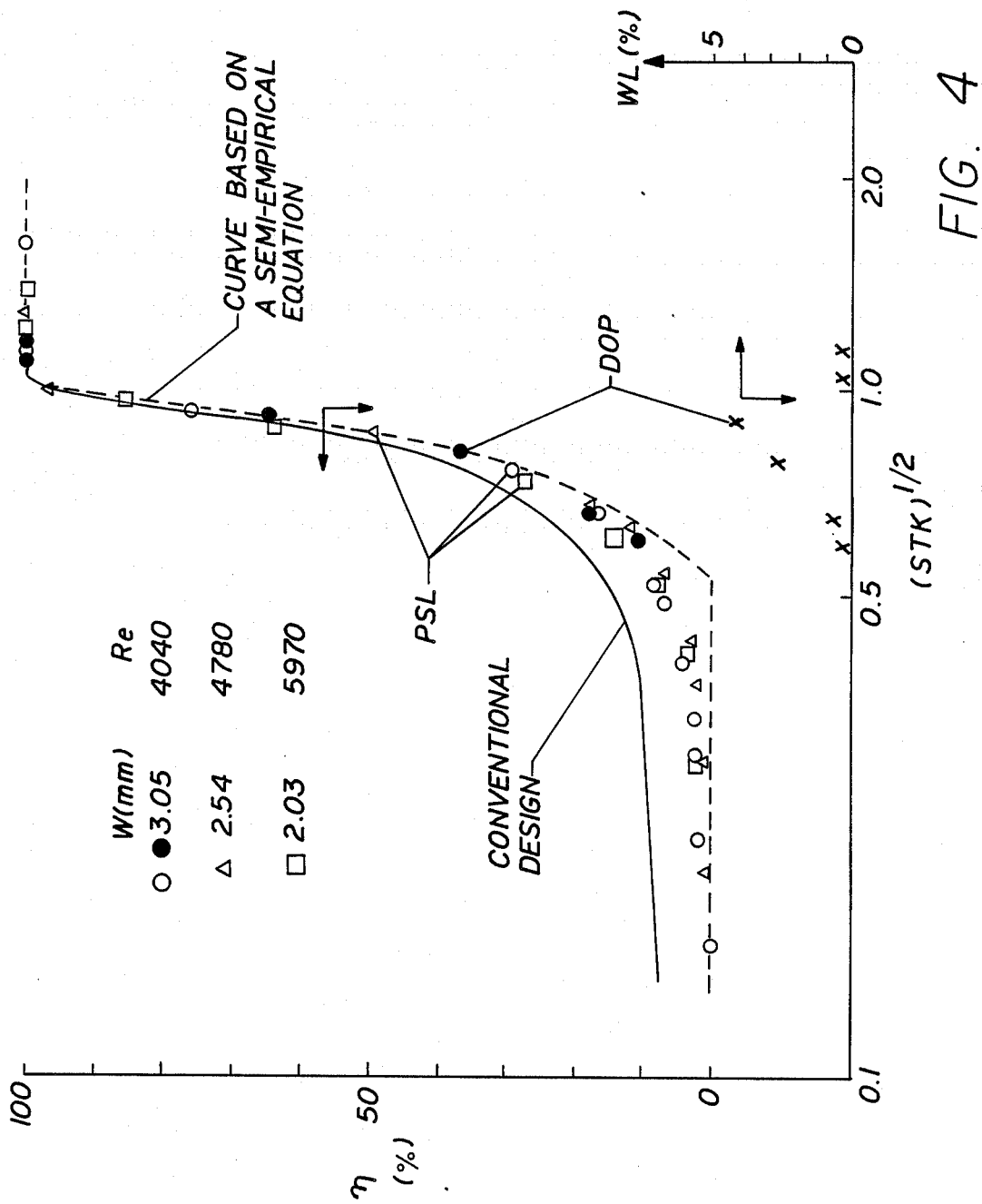
FIG. 4 is a plot of the separation efficiency curves and internal wall losses, around the cutoff sizes, of the improved virtual impactor for both polystyrene latex and dioctyl phthalate aerosols.

FIG. 4 shows the separation efficiency curves and internal wall losses, around the cutoff sizes, of impactors having a W of 3.05 mm, 2.54 mm, and 2.03 mm at minor flow ratios and clean air ratios of 8% and 18%, respectively, for PSL and liquid DOP aerosols, compared to conventional virtual impactor design. The dashed line curve is based on a semi-empirical equation from Masuda, et al., supra.

Based on the foregoing experiments and design analysis, an improved virtual impactor having an inner wall surface to linear axis angle of 30 degrees, with little internal loss had the following dimensional characteristics where W was 3.05 mm:

$W_1 = 3.0\ W$
$W_2 = 6.5\ W$
$W_3 = 3.0\ W$
$T = 1.0\ W$
$S = 1.0\ W$
$D_1 = 1.5\ W$
$D_2 = 3.0\ W$
$t = 1.0\ W$
$R = 0.3\ W$

For other desired cutoff particle size, $D_{AE,50}$, and total flow rate, $Q_T$, the nozzle diameter, W, can be estimated as follows:

$$W\ (mm) = 0.56\ D_{AR,50}^{\frac{3}{2}}\ (\mu m)\ Q_T^{\frac{1}{2}}\ (L/min),$$

$$D_{AR,50} = D_{AE,50}\ [C(D_{AE,50})]^{\frac{1}{2}}$$

where $D_{AR}$ is the aerodynamic resistance diameter (Raabe, "Aerosol Aerodynamic Size Conventions for Inertial Sampler Calibration", Air pollution Control Assoc. J., Vol. 26, No. 9, pp. 856–860, 1976), $C(D_{AE})$ the slip correction factor for a particle of aerodynamic diameter $D_{AE}$, and subscript 50 indicates the cutoff value at 50% separation efficiency.

We claim:

1. In a virtual impactor for separating solid or liquid particulate matter in an aerosol flow into a coarse particle flow and a fine particle flow, the virtual impactor having an acceleration nozzle and a collection probe, each aligned about a predetermined linear axis, and a flow separation region therebetween; said acceleration nozzle comprising an inlet, a substantially narrower outlet orifice, and a flow focusing portion therebetween formed with an inner wall surface for flow of said aerosol adjacent thereto and shaped for converging said aerosol flow from said inlet toward the linear axis whereby said converged aerosol flows through said outlet orifice through said flow separation region; said collection probe having an inlet impaction opening centered on said linear axis; the improvement comprising:

means for flowing gas of near zero or zero aerosol content into the center of said aerosol flow as a core of gas that converges with said aerosol flow and flows therewith through the outlet orifice of said nozzle encased by said aerosol while maintaining aerosol flow adjacent the inner wall surface of said focusing portion.

2. The improvement of claim 1 in which said means for flowing core gas provides a flow rate of core gas that is at least 1.2 times the rate of said coarse particle flow.

3. The improvement of claim 1 in which the inlet opening of said collection probe is formed with an annular inner wall surface, the ratio of the length thereof to the inner diameter of the nozzle outlet orifice at said separation region being at least 0.3.

4. The improvement of claim 1 in which the collection probe is annular and the ratio of the outer diameter of said collection probe at said separation region to the inner diameter of the nozzle outlet orifice at the separation region is less than 5.

5. The improvement of claim 1 in which the impaction opening of said collection probe is defined by a rounded shoulder, the ratio of the radius of said shoulder to the inner diameter of the nozzle output orifice at the separation region being at least 0.1.

6. The improvement of claim 1 in which the ratio of the outer diameter of said nozzle to the inner diameter of the nozzle outlet orifice at said separation region is less than 5.

7. The improvement of claim 1 in which the angle of the inner wall surface of the focussing portion of said nozzle relative to said linear axis is in a range of about 20 degrees to about 60 degrees.

8. The improvement of claim 1 in which the ratio of the inner diameter of said collection probe at said separation region to the inner diameter of the nozzle outlet orifice at said separation region is in a range of at least 1 to about 1.8.

9. The improvement of claim 1 in which the ratio of the length of said flow separation region to the inner diameter of the nozzle outlet orifice thereat is in the range of 0.5 to about 1.5.

10. The improvement of claim 1 in which the outlet orifice of said acceleration nozzle is formed with an annular inner wall surface, the ratio of the length thereof to the inner diameter of the nozzle outlet orifice at said separation region being in the range of about 0.5 to about 1.5.

11. The improvement of claim 1 in which laminating means are disposed in the inlet of said acceleration nozzle for laminar flow therethrough of said aerosol, said core flow means comprising conduit for said core gas protruding into said acceleration nozzle inlet downstream of said laminating means, said laminating means being centered on said core gas conduit.

12. The improvement of claim 1 in which said core gas is air.

13. The improvement of claim 1 in which said core gas is purified inert gas.

14. In a virtual impactor for separating solid or liquid particulate matter in an aerosol flow into a coarse particle flow and a fine particle flow, the virtual impactor having an acceleration nozzle and an annular collection probe, each aligned about a linear axis, and a flow separation region therebetween; said acceleration nozzle comprising an inlet, laminating means disposed in said inlet for laminar flow therethrough of said aerosol, an outlet orifice that is substantially narrower than said inlet and formed with an annular inner wall surface, and a flow focusing portion therebetween formed with an inner wall surface, having an angle relative to said linear axis in the range of about 20 degrees to about 60 degrees for flow of said aerosol adjacent thereto and for converging said aerosol flow from said inlet toward said linear axis whereby said converged aerosol flows through said outlet orifice to said flow separation region; said collection probe having an inlet impaction opening defined by a rounded shoulder and formed with an annular inner wall surface centered on said linear axis; the improvement comprising:

core flow means comprising a conduit for flowing gas that is substantially free of aerosol in the center of said aerosol flow downstream of said laminating means at a flow rate that is at least 1.2 times the rate of said coarse particle flow, said laminating means being centered on said gas conduit to converge said core gas with said aerosol flow to flow therewith through the outlet orifice of said nozzle as a core encased by said aerosol while maintaining aerosol flow adjacent the inner wall surface of said focusing portion, the ratio of the following dimensions to the inner diameter of the nozzle outlet orifice at said separation region being as follows:

length of the annular inner wall surface of the collection probe = at least 0.3, outer diameter of the collection probe at said separation region = less than 5.

radius of the rounded shoulder of the impaction opening of the collection probe = at least 0.1, and outer diameter of the nozzle outlet orifice at the separation region = less than 5.

15. The improvement of claim 14 in which the ratio of the following dimensions to the inner diameter of the nozzle outlet orifice at said separation region is as follows:

inner diameter of the collection probe at the separation region = at least 1 to about 1.8, length of the flow separation region = about 0.5 to about 1.5, and length of the annular inner wall surface of the outlet orifice of the accelerator nozzle = about 0.5 to about 1.5.

16. The improvement of claim 1 or 14 in which the inner diameter W, in millimeters, of the nozzle outlet orifice at said separation region is approximately given by $$W = 0.56\, D_{AR,50}^{3/2}\, Q_T^{1/2}$$

wherein $Q_T$ is the total flow rate in liters per minute and $$D_{AR,50} = D_{AE,50}\, [C(D_{AE,50})]^{1/2}$$

where $D_{AR}$ is the aerodynamic resistance diameter in micrometers, $C(D_{AE})$ is the slip correction factor for a particle of aerodynamic diameter $D_{AE}$, and subscript 50 indicates the cutoff value at 50% separation efficiency.

* * * * *

UNITED STATES PATENT AND TRADEMARK OFFICE
CERTIFICATE OF CORRECTION

PATENT NO. : 4,767,524

DATED      : August 30, 1988

INVENTOR(S) : Yeh, Chen, Cheng and Newton

It is certified that error appears in the above-identified patent and that said Letters Patent is hereby corrected as shown below:

Col 3, line 67, "8" should be --3--.

Col. 4, line 58, "86" should be --36--.

Col. 5, line 18, "86" should be --36--.

Col. 6, line 36, "R = O.3 W" should be --R = 0.3 W--.

(for clarification, the letter "O" should be "0" zero .)

Col. 6, line 46, "surfece" should be --surface--.

Signed and Sealed this

Seventh Day of March, 1989

*Attest:*

DONALD J. QUIGG

*Attesting Officer*    *Commissioner of Patents and Trademarks*